United States Patent [19]
Gioffre et al.

[11] Patent Number: 4,826,676
[45] Date of Patent: May 2, 1989

[54] ANTICARIOGENIC AND ANTICALCULUS COMPOSITIONS CONTAINING ZEOLITIC ZINC CATIONS

[75] Inventors: Anthony J. Gioffre, Ridgefield, Conn.; Bonita K. Marcus, Rye, N.Y.

[73] Assignee: UOP, Des Plains, Ill.

[21] Appl. No.: 67,821

[22] Filed: Jun. 30, 1987

[51] Int. Cl.$^4$ ............................................. A61K 7/18
[52] U.S. Cl. ......................................... 424/52; 424/49
[58] Field of Search ..................................... 424/49–58

[56] References Cited

U.S. PATENT DOCUMENTS

| 4,022,880 | 5/1977 | Vinson et al. | 424/49 |
|---|---|---|---|
| 4,132,771 | 1/1979 | Schreiber et al. | 424/49 |
| 4,144,332 | 3/1979 | Lamberti | 424/54 |
| 4,159,316 | 6/1979 | Januszewski et al. | 424/49 |
| 4,193,987 | 3/1980 | Harth et al. | 424/49 |
| 4,349,533 | 9/1982 | Dent et al. | 424/49–58 |
| 4,592,285 | 6/1986 | Gioffre et al. | 252/89.1 |

Primary Examiner—Shep K. Rose
Attorney, Agent, or Firm—Richard G. Miller

[57] ABSTRACT

The anticariogenic activity of fluorine-containing compounds in oral compositions also containing zeolitic zinc ions is retained at advantages levels over protracted periods of time by adjusting the pH of the composition to the range of 9.5 to 11. The zeolite not only provides desired $Zn^{++}$ ions to the formulation with minimal adverse affect on the active fluoride content but also is found to be an exceptionally good abrasive and/or polishing agent.

4 Claims, No Drawings

ANTICARIOGENIC AND ANTICALCULUS COMPOSITIONS CONTAINING ZEOLITIC ZINC CATIONS

BACKGROUND OF THE INVENTION

1. Field of the Invention

The present invention relates in general to stable compositions for inhibiting dental plaque and calculus formation and more particularly to oral compositions containing a combination of active zinc in the form of zeolitic zinc ions and fluoride ions. The invention particularly relates to toothpaste compositions having the aforesaid characteristics.

The presence of zinc compounds in oral products has been recognized for many years as beneficial for a variety of reasons. Zinc oxide and zinc phosphate were proposed as stabilizers in dental creams in U.S. Pat. No. 3,622,662 issued in November 1971 In U.S. Pat. No. 3,095,396 it is proposed to incorporate zinc salts into dentifrice formulations to inhibit the dissolving action of sodium metaphosphate. More recently, the zinc ion has been found to inhibit the formation of plaque and its consequent calcification to form calculus (tartar). Combination of zinc salts with enzymes, with antibacterial agents and with tetradecylamine are disclosed in U.S. Pat. Nos. 4,082,841; 4,022,880; and 4,146,607, respectively, for such purposes. Zinc carboxymethyloxysuccinate is utilized for its antiplaque and anticalculus properties in compositions proposed in U.S. Pat. No. 4,144,323.

For a period of many years, however, it was believed that zinc salts were only effective if present in dental formulations having pH values which are distinctly acidic in order to prevent the formation of the nearly insoluble, and thus ineffective, zinc hydroxide. The zinc ion itself tends to impart an organoleptically unpleasant astringency to dentifrices and other oral compositions, and when coupled with the sour taste characteristic of acidic compositions, the unpleasant taste was not readily tolerated. In efforts to avoid the disadvantages of zinc salts, it has more recently been found that the addition of glycine (aminoacetic acid) to oral compositions containing zinc salts permits the ambient pH to be increased to a range of 4.5 to 8.0, thus avoiding much of the astringency previously experienced while maintaining the zinc in a biologically active form. Such compositions are disclosed in U.S. Pat. No. 4,339,432 issued July 13, 1982 to Ritchey et al.

A still more recent advance has been made by the introduction of the zinc ions into oral compositions in the form of crystalline zinc aluminosilicates, i.e., zinc-exchanged zeolites. Not only is the biologically active zinc effectively provided by in situ ion exchange, but also other functions important to dental compositions such as abrasion of plaque and polishing as well as the creation of localized warmth by rehydration can be provided by the same constituent, thereby making formulation easier. A discussion of the benefits of using zeolites with therapeutic metal cations including zinc is set forth in U.S. Pat. No. 4,349,533 issued Sept. 14, 1982 to A. L. Dent et al. The use of zeolites in the alkali metal or ammonium cation form as anticorrosive agents is also described in U.S. Pat. No. 4,193,987.

In addition to antiplaque and anticalculus agents, it has for many years been the widely accepted practice to include in dentifrice and other oral compositions an anticariogenic agent, especially a water soluble fluorine-containing anticariogenic material. It is desirable to employ a sufficient quantity of the fluorine compound such that the concentration as the soluble fluoride in the dentifrice is from 600 to 1000 ppm (weight). Typically, the fluoride compound is sodium fluoride (NaF), stannous fluoride ($SnF_2$) or sodium monofluorophosphate ($Na_2PO_3F$). Ideally the formulation of the dentifrice is such that essentially all of the fluorine compound employed is able to provide all of its fluorine value in the form of effective fluoride ion so that the total fluorine content of the dentifrice can be kept at a minimum and still provide the degree of anticariogenic activity essential for good dental health. Excessive amounts of fluorine can be seriously toxic when ingested, the degree of toxicity varying considerably among the various fluorine compounds.

SUMMARY OF THE INVENTION

The present invention resides in a toothpaste formulation for the care of the mouth or teeth, particularly for preventing or inhibiting plaque formation, paradentosis or caries consisting essentially of a polishing agent, a source of biologically active fluoride ions and a source of biologically active zinc ions, the improvement comprising utilizing as at least 10—% of the polishing agent a zinc-exchanged form of zeolite Y having a $SiO_2/Al_2O_3$ molar ratio in the range of from 2.5 to 10, preferably 3 to 6, said composition having a pH value of at least 9.5, and preferably from 9.5 to 11.

DETAILED DESCRIPTION OF THE INVENTION

We have now discovered that although essentially any zeolite species which has a $SiO_2/Al_2O_3$ of less than about 10 is capable, when adequately ion-exchanged with zinc ions, of imparting the required concentration of zinc ions to dentifrice compositions, it has surprisingly been found that there is a vital correlation between the pH value of the composition containing both the zinc zeolite and the fluoride source and the retention of effective amounts of soluble fluoride over the period of time required to package, distribute and utilize the dentifrice composition—usually a period of at least about 9 weeks. This finding is particularly surprising since it has been proposed to use other cation forms of zeolites as polishing agents in dentifrice formulations which can contain anticariogenic, i.e., active, fluorine compounds. In U.S. Pat. No. 4,209,504, for example, all zeolites in the sodium cation form, and sodium zeolite A particularly, are proposed as polishing agents, in large measure because the zeolites were found to be compatible with the active substances of toothpastes. This was found to be particularly true with respect to ionic or complex-bound fluorine where excellent compatibility with the zeolite was alleged. That allegation is supported by Kato et al., Reports of the Institute for Medical and Dental Engineering, 3, 22-35 (1969) wherein crystalline zeolites as diverse in structure as clinoptilolite, mordenite and synthetic faujasites in the sodium and/or calcium forms when admixed in aqueous slurries with NaF, did not result in a variation of the $F^-$ ion concentration with the passage of time. In the case of the synthetic faujasite materials, the $F^-$ ion concentration was said to be little changed even after a period of four months In the introduction of zinc ions into toothpaste formulations by means of a zinc ion exchanged zeolite it would be expected that the zeolite species employed could be any of those previously employed in the sodium cation form principally as polishing agents. Thus all that should be required to provide zinc ions to such formulations is to exchange at least a part of the sodium cations of sodium zeolite A or sodium zeolite X for zinc ions and then utilized the resulting ZnA or ZnX in the manner taught by Harth et al. (U.S. Pat. No. 4,209,504). By far the most commonly used zeolites in oral compositions are zeolite A and zeolite X. These zeolites, in acid modified forms, are preferred by Dent et al. for use in the toothpaste formulations disclosed in U.S. Pat. No. 4,349,533, although zeolites generally are said to be useful, including zeolite Y. According to Dent et al., the zeolites, in addition to being acid modified, can also be in the calcium, magnesium or zinc cationic forms. Zeolite $P_c$, the cubic crystal form of synthetic zeolite B, has been found to have a crystal morphology which makes it especially useful as a polishing agent.

For reasons not yet elucidated, we have found that the zinc cation of zeolites having a relatively large proportion of framework $AlO_2$ tetrahedral units, i.e. having $SiO_2/Al_2O_3$ framework molar ratios of less than ten, cause an unacceptable reduction in water-soluble fluoride content in aqueous oral formulations when the pH is less than 9.5. This correlation of pH value with the presence of zinc cations is established by the test data reported in the Examples appearing below.

EXAMPLE 1

(a) Twenty-five grams of the test sample zeolite was added to 100 ml. of a water solution of sodium fluoride in which the NaF concentration was 1,000 ppm (weight) and agitated by means of a wrist action shaker for 24 hours at ambient room temperature. A sample of the aqueous medium was then withdrawn through a 0.45 micron millipore syringe filter and analyzed chemically for $F^-$. The results are shown in tabular form below:

TABLE I

| Solution Tested | pH | $F^-$ Content, ppm (weight) |
|---|---|---|
| NaF Solution (no zeolite) | | 995* |
| NaF Solution + $ZnP_c$ | 6.75 | 110 |
| NaF Solution + ZnA | 6.96 | 120 |
| NaF Solution + ZnY | 6.91 | 300 |
| NaF Solution + ZnX | 6.8 | 380 |
| NaF Solution + NaA | 10.8 | 1,000 |

*Average of two runs (b) To test the effects of lowering the pH of the NaF solution while in contact with a ZnP zeolite, slurries were prepared using 100 ml of the NaF solution of part (a), 25 grams of the ZnP of part (a) either with ZnA or various amounts of sodium carbonate. The pH values and the residual $F^-$ concentration of the aqueous medium after 24 hours in contact with the zeolite and/or base in each case are shown in Table II below:

TABLE II

| Solution Resulting from Treatment with: | pH | $F^-$ Content, ppm (weight) |
|---|---|---|
| ZnP + 25 g $Na_2CO_3$ | 10.28 | 700 |
| ZnP + 14.15 g $Na_2CO_3$ | 9.05 | 400 |
| ZnP + 10.4 g $Na_2CO_3$ | 8.15 | 100 |
| ZnP + 25 g NaA | 8.39 | 100 |

EXAMPLE 2

To determine the suitability of aqueous compositions containing soluble fluoride ion and zeolites in the zinc cation form, a number of 25 gram samples of zinc zeolite P and zinc zeolite Y containing different concentrations of $Zn^{++}$ cations were placed in 8-ounce plastic containers together with 100 ml. of an aqueous solution of sodium fluoride having an $F^-$ ion concentration of 1000 ppm. In half of the containers there was also added 25 grams of STPP (sodium triphosphate, $Na_5P_3O_{10}$) which raised the ph of the overall composition to above 9.5. The containers were sealed and placed on a wrist-action shaker for 24 hours, and then placed in a 120° C. oven for various periods of time up to 9 weeks. Liquid samples were collected from the containers by filtration through a 0.45 micron millipore syringe filter, and the collected samples analyzed ro fluoride ion content. The results are shown below in Table III. The zeolite samples are designated by the $ZnO/Al_2O_3$ molar ratio, the structure type and the $SiO_2/Al_2O_3$ molar ratio, i.e. "(0.44)ZnP(2.45)" indicates a ZnP zeolite having a $SiO_2/Al_2O_3$ molar ratio of 2.56 and a $ZnO/Alhd 2O_3$ ratio of 0.44.

TABLE III

| Sample Type | Initial pH | Week 3 pH | Week 3 ppm $F^-$ | Week 6 pH | Week 6 ppm $F^-$ | Week 9 pH | Week 9 ppm $F^-$ |
|---|---|---|---|---|---|---|---|
| $F^-$ Solution (1000 ppm) | | 7.17 | 1000 | | | | |
| (1.6) ZnP (2.56) | 6.48 | 5.70 | >100 | | | | |
| (1.6) ZnP (2.56) | 9.70 | 9.98 | 700 | 10.14 | 700 | 10.06 | 700 |
| (.44) ZnP (2.45) | 7.81 | 7.48 | 200 | | | | |
| (.44) ZnP (2.45) + 25 grams STPP | 9.52 | 10.49 | 800 | 10.80 | 900 | 10.67 | 800 |
| (1.04) ZnY (4.88) | 6.33 | 5.97 | 400 | | | | |
| (1.04) ZnY (4.88) + 25 grams STPP | 9.86 | 10.07 | 800 | 10.24 | 800 | 10.08 | 800 |
| (.56) ZnY (5.07) | 6.78 | 6.83 | 200 | | | | |
| (.56) ZnY (5.07) + 25 grams STPP | 10.05 | 10.07 | 900 | 10.23 | 900 | 10.24 | 900 |

As is readily apparent from the foregoing data, only those compositions which had pH values greater than 9.5 contained adequate soluble fluoride after 9 weeks.

As essential ingredients, the oral compositions of the present inventions comprise from 10 to 40 weight percent of a solid abrasive or polishing agent of which at least 10 percent is a zinc ion-exchanged zeolite having a $SiO_2/Al_2O_3$ molar framework ratio of less than 10; at least 1000 ppm fluoride ion derived from a water-soluble source and water in at least a sufficient amount to form an aqueous matrix. The pH of the composition is adjusted by the addition of bases or buffering agents to a value of at least 9.5, and preferably between 9.5 and 11. The compositions can optionally contain the customary fillers, flavors, thickeners, surface active agents and the like.

Illustrative of the polishing agents which may be employed in addition to the zinc zeolites are impalpable phosphates, e.g., dicalcium phosphate, tricalcium phosphate, insoluble sodium metaphosphate, magnesium phosphate, calcium pyrophosphate, crystalline silica, colloidal silica, aluminum hydroxide, alumina trihydrate, magnesium carbonate, calcium carbonate, bentonite, talc, calcium silicate, calcium aluminate, and aluminum oxide. The various polishing agents are described in standard handbooks such as Sagarin, "Cosmetics: Science and Technology," Interscience Publishers, Inc. (1963).

Suitable flavoring or sweetening agents or mixture thereof, if any, may be employed in formulating a flavor for the effervescent compositions of the present invention. Examples of suitable flavoring constituents include the flavoring oils, e.g., oils of spearmint, peppermint, wintergreen, sassafras, clove, sage, eucalyptus, marjoram, cinnamon, lemon, lime, grapefruit and orange as well as flavoring aldehydes, esters such as methyl salicylate, alcohols, and higher fatty compounds known in the art. Also useful are such chemicals as menthol, carvone and anethole. Of these, the most commonly employed are the oils of peppermint, spearmint, and eucalyptus, and anethole, menthol and carvone. In some cases flavorful solvents, such as chloroform and mock chloroform, may be employed. Such flavorings may be used as liquids or may be solidified by being mixed with a particulate carrier material, such as starch, calcium carbonate, paraffin, vegetable wax, fat, higher fatty acid or other suitable carrier substances. In the cases of solid flavors, such as vanillin, sage, citric acid or licorice, the flavor may be converted to liquid form, if so desired, by dissolving it in the solvent or emulsifying it, usually with the help of a synthetic or natural emulsifying agent. The choice as to whether to utilize particulate solid or liquid flavors or to convert such flavors to a particulate solid or liquid form, respectively, will often depend on the properties desired in the flavor and its compatibility with the sweetener and any other material to be present with it. Suitable sweetening agents include mannitol, sucrose, lactose, maltose, sorbitol, xylitol, sodium cyclamate, saccharin, the dipeptides of the U.S. Pat. No. 3,939,261 and the oxathiazin salts of U.S. Pat. No. 3,932,606. Suitably, flavor and sweetening agent may together comprise from about 0.1 to 10% or more of the compositions of the instant invention.

The compositions of this invention include liquids and solids that may be proportioned to form a creamy mass of desired consistency which is extrudable from an aerosol or other pressurized container or a collapsible tube (for example aluminum, aluminum alloy or plastic). In general, the liquids in a cream formulation will comprise chiefly glycerine or an oil, propylene glycol, polyethylene glycol 400, etc., including suitable mixtures thereof. The total liquid content will generally be about 20 to 75 percent by weight of the composition. A gelling agent in cream formulations and gels may be employed, such as the natural and synthetic gums and gum-like materials, for example, Irish moss, gum tragacanth, methyl cellulose, polyvinylpyrrolidone, hydrophilic colloidal carboxyvinyl polymers such as those sold under the trademark Carbopol 934 and 940, hydroxyethyl cellulose, Indian gum, acacia gums, agar agar, locust bean gum, synthetic silicated clays such as those sold under the trademark Laponite CP and Laponite SP, pectin and finely divided pyrogenic silica, sold under the trademarks Cab-O-Sil M5, Syloid 244, Syloid 266 and Aerosol D 200.

The proportions of gelling agents or thickeners in extrudable effervescent compositions are sufficient to form an extrudable, shape-retaining product which can be squeezed from a tube and substantially maintain its shape thereon. In most cases, no more than 10% of gelling agent need be used and in most instances about 0.5 to 10% will suffice, and preferably about 1 to 5%.

Suitable oils for use in forming the present compositions include those which have viscosities ranging from about 100 to about 300 centipoises at 70° F. Oils employable herein include mineral oil, light liquid petrolatum thickened to the necessary viscosity; and vegetable oils. A mineral oil commonly employed in cosmetic compositions is Mineral Oil U.S.P. also known as Liquid Petrolatum U.S.P, mineral oil (heavy medicinal) white mineral oil, liquid paraffin, and heavy liquid petrolatum. Mineral oil U.S.P. is defined in Remington's Pharmaceutical Sciences, 13th edition, Mack Publishing Co., Easton, Pa. 1965 as "a mixture of colorless transparent, oily liquid, free or nearly free from fluorescence." It is tasteless and odorless when cold and develops not more than a faint odor of petroleum when heated.

A light liquid petrolatum employable herein is Light Liquid Petrolatum N.F. also known as light liquid paraffin and light white mineral oil. It is described in Remington s Pharmaceutical Sciences, as " . . . a mixture of liquid hydrocarbons obtained from petroleum, it may contain a stabilizer." If Light Liquid Petrolatum N.F. is used as the oil it may be thickened to the desired viscosity of from about 100 to about 300 centipoises at 70° F. with one of the well known commercially available inert thickening materials, such as a pyrogenic silica sold under the trademark Cab-O-Sil, or a hydrogenated castor oil, sold under the tradename THIXIN.

Suitable vegetable oils which may be used as the oil ingredient include coconut oil, cotton-seed oil, sesame oil and similar non-toxic vegetable oils, as described in Vegetable Fats and Oils by E. W. Eckey, Reinhold Publishing Corp., New York 1954. The vegetable oil is desirably selected to fall within the viscosity range of from about 100 to about 300 centipoises. A particular vegetable oil falling within this range is NEOBFE M-5, a fractional trigylceride of coconut oil. The vegetable oil ingredient may contain a minor amount of an antioxidant such as butylated gydroxyanisole or butylated hydroxytoluene, preferably in an amount ranging from about 0.1% to about 3% by weight, based on the weight of the vegetable oil employed.

Organic surface active agents usually are selected from the classes of anionic, nonionic and amphoteric surface active agents, but cationic detergents can be employed. The anionic detergents include long chain fatty or poly lower alkoxy groups plus hydrophilic radicals, and are usually employed in the form of water soluble salts. A more detailed description is contained in Schwartz et al., *Surface Active Agents,* Vol II (1958). The nonionics include those containing chains of lower alkylene oxide, e.g., ethylene oxide and propylene oxide in which there are present from 10 to 100 or more moles of lower alkylene oxide. The amphoteric or ampholytic agents include quaternized imidazole derivatives such as Miranol $C_2M$.

The proportions of materials which are usually employed to obtain the properties described in the preceding paragraphs can vary over a wide range, but are generally from 5 to 50% polishing agent, 0.5 to 5 percent gelling agent or thickener, 30 to 85% of polyhydric alcohol, 5 to 30% water, 0.5 to 5% detergent and 600 to 1000 ppm soluble fluoride ion. A typical formulation for a toothpaste composition in accordance with the present invention is as follows:

| Constituent | Parts by Weight |
| --- | --- |
| Glycerol | 25 |
| Sodium carboxymethyl cellulose | 0.6 |
| Sodium benzoate | 0.5 |
| Sorbitol (70% aqueous solution) | 44 |
| Water | 3.8 |
| Sodium Saccharin | 0.2 |
| Pyrogenic silica | 2.0 |
| Silica aerogel | 4.0 |
| ZnY ($SiO_2/Al_2O_3$ = 4.8) | 16 |
| Sodium lauryl sulfate | 2.0 |
| Essential Oils (Flavor) | 1.5 |
| NaF | |

Type Y zeolites are particularly preferred for use in the in the practice of the present invention. Such zeolites can be, insofar as the $SiO_2/Al_2O_3$ molar ratios are from greater than 3 to 6, prepared by conventional ion-exchange with an aqueous zinc salt solution of an as synthesized NaY prepared according to the procedures described in detail in U.S. Pat. No. 3,130,007 issued Apr. 21, 1964. For ZnY compositions having $SiO_2/Al_2O_3$ molar ratios greater than 6 up to 10, the zinc ion exchange can be carried out using a form of zeolite Y which has been subjected to dealumination procedures well known in the art. For example, high temperature steaming treatments which result in dealumination are reported by P. K. Maher et al. in "Molecular Sieve Zeolites", Advan. Chem. Ser. 101, American Chemical Society, Washington, D.C., 1971, p.266. A more recently reported procedure, especially useful for increasing the $SiO_2/Al_2O_3$ of zeolite Y, involves dealumination and the substitution of silicon into the dealuminated lattice sites. This process is disclosed in U.S. Pat. No. 4,503,023 issued Mar. 5, 1985 to Skeels et al.

The fluorine compounds suitably employed in the compositions of the present invention are any of those conventionally used in oral compositions as anticariogenic agents. These include the various salts of monofluorophosphorec acid, particularly sodium, potassium, lithium, calcium and aluminum mono and difluorophosphates, and the various fluorides containing fluorine in ion-bound form such as sodium, lithium, potassium and ammonium fluorides, stannous fluoride, manganese fluoride, zirconium fluoride, aluminum fluoride, zinc fluoride, germanium fluoride, palladium fluoride, titanium fluoride, alkalifluorozirconates, e.g. sodium or potassium fluorozirconate, stannous fluorozirconate, fluoroborate or fluorosulfate, e.g. sodium or potassium fluorosulfate. Organic fluorine compounds can also be used, particularly the known addition products of long-chain amines or amino acids and hydrogen fluoride, monoethanolaminohydrofluoride or methyltriethyl ammonium fluoride. Particularly preferred fluorine compounds are stannous fluoride, sodium fluoride and sodium monofluorophosphate.

What is claimed is:

1. In an aqueous toothpaste formulation comprising a polishing agent, a source of soluble fluoride ions and a source of of biologically active zinc ions, the improvement which comprises utilizing as at least 10 percent by weight of the polishing agent a zinc-exchanged zeolite having a $SiO_2/Al_2O_3$ molar ratio of from 2.5 to 10 and adjusting the pH of the composition to be greater than 9.5.

2. Composition according to claim 1 wherein at least 20 percent of the framework $AlO_2^-$ tetrahedral units of the zinc exchanged zeolite are associated with zinc cations.

3. Composition according to claim 1 wherein the pH of the composition is adjusted to be within the range of 9.5 to 11.

4. Composition according to claim 3 wherein the zinc-exchanged zeolite is zeolite Y having a $SiO_2/Al_2O_3$ molar ratio of from 3 to 6.

* * * * *